United States Patent
Yamamoto

(10) Patent No.: US 9,212,384 B2
(45) Date of Patent: Dec. 15, 2015

(54) MICROBIAL CULTURE MEDIUM AND MICROBIAL CULTURE METHOD USING ACID/ACTIVATED CLAY

(75) Inventor: Hiroaki Yamamoto, Ibaraki (JP)

(73) Assignee: TSUMARA & CO., Tokyo (JP)

( * ) Notice: Subject to any disclaimer, the term of this patent is extended or adjusted under 35 U.S.C. 154(b) by 905 days.

(21) Appl. No.: 12/442,773

(22) PCT Filed: Sep. 25, 2007

(86) PCT No.: PCT/JP2007/068537
§ 371 (c)(1),
(2), (4) Date: Jun. 2, 2009

(87) PCT Pub. No.: WO2008/038625
PCT Pub. Date: Apr. 3, 2008

(65) Prior Publication Data
US 2010/0062515 A1    Mar. 11, 2010

(30) Foreign Application Priority Data

Sep. 28, 2006  (JP) .................................. 2006-265622

(51) Int. Cl.
*G01N 33/53*   (2006.01)
*C12Q 1/04*    (2006.01)
*C12N 1/20*    (2006.01)

(52) U.S. Cl.
CPC . *C12Q 1/045* (2013.01); *C12N 1/20* (2013.01)

(58) Field of Classification Search
CPC ..................................................... C12Q 1/045
USPC ......................................................... 435/7.2
See application file for complete search history.

(56) References Cited

U.S. PATENT DOCUMENTS 5,314,855 A    5/1994    Thorpe et al.

FOREIGN PATENT DOCUMENTS

| JP | 51-48481 A | 4/1976 |
| JP | 06-178695 A | 6/1994 |
| JP | 06-210167 A | 8/1994 |
| JP | 2003-310296 A | 11/2003 |

OTHER PUBLICATIONS

Diaz et al. (2001) Studies on the acid activation of Brazilian smectitic clays. Quimica Nova 24(3): 345-353.*
Campbell et al. "Effect of bentonite clay on the growth of Gaeumannomyces graminis var. tritici and on its interactions with antagonistic bacteria", J of General Microbiology, 1983, 129:771-777.*
Rollinger et al. "Survival of selected bacterial species in sterilized activated carbon filters and biological activated carbon filters", Applied and Environmental Microbiology, 1987, 53(4):777-781.*
Flessner et al. J of Molecular Catalysis A: Chemical, 2001, 168:247-256.*
"The Present Condition of Microbiological Quality Assurance of Crude Drug/Kampo Formulations", J. Antibact, Antifung, Agents vol. 25, No. 8 (1997) pp. 467-473.
"Detection of colon bacillus, *Salmonella* and golden staph", Bokin Bobai, vol. 31, No. 9 (2003) pp. 517-525.
Notice of Reasons for Refusal dated Apr. 30, 2013, issued in counterpart Japanese Patent Application No. 2008-536373.
A. Hirokawa, "Characteristics and Applications of the Acid-treated 'Acid Clay'," Clay Science, v. 20, pp. 99-106 (1980).
R. Mokaya and W. Jones, "Acid Activation of Clays and Effect on Adsorption Properties," Ion Exchange Processes: Advances and Applications, University of Cambridge, Cambridge, U.K., pp. 243-252 (1993).
Zhao, et al., "Characteristics of Clay Minerals of Montmorillonites in the Wet State," Nippon Kagaku Kaisha, No. 2, pp. 209-215 (1989).
Office Action mailed Oct. 2. 2012, issued in Japanese Patent Application No. 2008-536373. Partial.

* cited by examiner

*Primary Examiner* — Bin Shen
(74) *Attorney, Agent, or Firm* — Sughrue Mion, PLLC

(57) ABSTRACT

There is provided a microbial culture medium and a microbial culture method for adequately growing a target bacterium contained in an antibacterial test sample.

The microbial culture medium for growing a target bacterium contained in an antibacterial test sample is composed of a basal medium for microbial culture, and acid clay or activated clay contained in the basal medium. The microbial culture method for growing a target bacterium contained in an antibacterial test sample using a microbial culture medium includes adding acid clay or activated clay to a solution of the test sample. It is preferred that the acid clay or activated clay be combined with activated carbon.

6 Claims, No Drawings

MICROBIAL CULTURE MEDIUM AND MICROBIAL CULTURE METHOD USING ACID/ACTIVATED CLAY

TECHNICAL FIELD

The present invention relates to a microbial culture medium and a microbial culture method (hereinafter may be referred to simply as "culture medium" and "culture method", respectively), and specifically to a microbial culture medium for growing a target bacterium contained in an antibacterial test sample, and a microbial culture method for growing a target bacterium contained in an antibacterial test sample.

BACKGROUND ART

It is known that the microbial limit test method described in Japanese Pharmacopoeia may not work for the microbial testing of Kampo crude drug products or microbial cells in the crude drugs as test samples, because target bacteria grow poorly in an ordinary commercial culture medium due to the presence of antibacterial substances (growth inhibitors) contained in the test sample.

In this case, Japanese Pharmacopoeia specifies that the influence of the antibacterial substance must be removed by any means such as dilution, filtration, neutralization, or inactivation. When the test sample is a preparation that is completely soluble in solvent, membrane filtration or the like is applicable, but if the test sample is insoluble matter, inactivation or dilution is the only means. Accordingly, there are few alternatives other than dilution.

For example, Non-Patent Document 1 describes that crude drugs and Kampo extracts have antibacterial activity, and Non-Patent Document 2 describes that cut or powdered crude drugs have antibacterial activity. However, these documents suggest no alternative for removal of antibacterial substances other than dilution.

In the cosmetics and pharmaceutical industries, inactivation of antibacterial substances is usually carried out through the addition of lecithin and polysorbate to the culture media. Culture media containing lecithin and polysorbate (for example, SCDLP medium) are commercially available, but such culture media are expensive and often not very effective for the inactivation of Kampo crude drug products, though they are highly effective for the inactivation of paraben-based and mercury-based preservatives.

Culture media containing activated carbon as an absorbent for adsorbing growth inhibitors are commercially available as special culture media. However, such culture media are not enough to remove antibacterial substances from Kampo crude drug products, crude drugs, or antibacterial foods such as spices.

Non-Patent Document 1: Bokin Bobai Vol. 25, No. 8, pp. 467-473, 1997

Non-Patent Document 2: Bokin Bobai Vol. 31, No. 9, pp. 517-525, 2003

DISCLOSURE OF INVENTION

Problems to be Solved by the Invention

In a microbial limit test on a Kampo crude product, crude drug, or antibacterial food such as a spice, repeated dilution of a test sample results in the decrease of sensitivity on the assumption that the test scale is the same. Therefore, problems with quality assurance, more specifically, risks such as economic losses caused by delivery of pseudo-negative products cannot be completely solved by the means. The problem with the dilution of the test sample also concerns other means for eliminating the influence of antibacterial substances.

In view of the above circumstances, the present invention is intended to provide a microbial culture medium and a microbial culture method for adequately growing a target bacterium contained in an antibacterial test sample.

Means for Solving the Problem

As a result of dedicated research to solve the above problems, the inventor has found that acid clay or activated clay, and further activated carbon added to a microbial culture medium or a solution used for the preparation of a test sample adsorb and reduces antibacterial substances contained in the test sample such as a Kampo crude product or crude drug, and thus repressing their antibacterial activity. The present invention has been accomplished on the basis of the finding.

More specifically, the microbial culture medium of the present invention is a microbial culture medium for growing a target bacterium contained in an antibacterial test sample, the microbial culture medium being composed of a basal medium for microbial culture, and acid clay or activated clay contained in the basal medium. The culture medium of the present invention preferably further contains activated carbon in the basal medium for microbial culture.

The microbial culture method of the present invention is a microbial culture method for growing a target bacterium contained in an antibacterial test sample using a microbial culture medium, the method including adding acid clay or activated clay to the solution of the test sample. The culture method of the present invention preferably further includes adding activated carbon to the solution.

Advantages

The present invention with the above-described aspects can provide a microbial culture medium and a microbial culture method for adequately growing a target bacterium contained in an antibacterial test sample such as a Kampo crude drug product, crude drug, or antibacterial food such as a spice, thereby facilitating the detection of the target bacterium contained in the test sample.

BEST MODE FOR CARRYING OUT THE INVENTION

Preferred embodiments of the present invention are described below in detail.

In the present invention, it is important that acid clay or activated clay is contained in the culture medium for growing the target bacterium contained in the antibacterial test sample, or in the solution of the test sample.

The acid clay or activated clay adsorbs the antibacterial substances contained in the test sample, which results in the repression of the antibacterial activity of the test sample and adequate growing of the target bacterium. As a result of this, the target bacterium is easily detected without being subjected to dilution or other known means. Acid clay referred herein is white or gray clay composed mainly of montmorillonite, and is a porous substance having a large specific surface area and adsorptivity. Activated clay is also a porous substance having a large specific surface area and adsorptivity equivalent to those of acid clay, and is produced by treating acid clay with a mineral acid. Since acid clay and activated clay are inexpensive, the present invention is markedly advantageous in terms of cost.

Specifically, the culture medium of the present invention is composed of a basal medium for microbial culture, and acid clay or activated clay contained in the basal medium. The loading of acid clay or activated clay depends on the type and properties of the test sample and target bacterium, and is preferably from 1 to 20% by weight, more preferably from 3 to 10% by weight of the culture medium. If the loading of the acid clay or activated clay is too small, the antibacterial activity may be insufficiently repressed, which can result in insufficient growth of the target bacterium and inaccurate detection of the bacterium. On the other hand, if the loading is excessive, further repression of the antibacterial activity cannot be expected.

In this case, the addition of activated carbon to the basal medium for microbial culture in combination with the acid clay or activated clay further represses the antibacterial activity thereby further promoting the growth of the target bacterium. The loading of the activated carbon depends on the type and properties of the test sample and target bacterium, and is preferably 1% by weight or more and less than 5% by weight, and particularly preferably from 1 to 3% by weight of the culture medium. If the loading of the activated carbon is less than 1% by weight, the growth of the target bacterium may not be markedly promoted, and not less than 5% by weight, the growth of the target bacterium may be hindered.

Specifically, according to the culture method of the present invention, acid clay or activated clay is added to the solution of the antibacterial test sample. The loading of acid clay or activated clay depends on the type and properties of the test sample and target bacterium, and is preferably from 1 to 20% by weight, more preferably from 3 to 10% by weight of the solution. If the loading of the acid clay or activated clay is too small, the antibacterial activity may be insufficiently repressed, which may result in insufficient growth of the target bacterium and inaccurate detection of the bacterium. On the other hand, if the loading is excessive, further repression of the antibacterial activity cannot be expected.

Also in this case, the addition of activated carbon to the solution in combination with acid clay or activated clay further represses the antibacterial activity thereby further promoting the growth of the target bacterium. The loading of the activated carbon depends on the type and properties of the test sample and target bacterium, and is preferably 1% by weight or more and 5% by weight or less, and particularly preferably from 1 to 3% by weight of the solution. If the loading of the activated carbon is less than 1% by weight, the growth of the target bacterium may not be markedly promoted, and if more than 5% by weight, the growth of the target bacterium may be hindered.

In the present invention, it is only important that acid clay or activated clay adsorbs the antibacterial substances contained in the test sample thereby removing the factors inhibiting the growth of the target bacterium from the test sample. The invention is not otherwise particularly limited as to the rest, and may be carried out according to a common procedure.

For example, the basal medium for microbial culture used in the present invention may be appropriately selected from common media such as those listed in Japanese Pharmacopoeia, in accordance with the test sample and target bacterium. For example, an SCD (soybean-casein-digest) broth medium may be used.

Examples of the antibacterial test sample to which the present invention is applicable include Kampo crude drug products, crude drugs, and antibacterial foods such as spices. The present invention is particularly useful for adequately growing target bacteria contained in these test samples, which cannot be sufficiently grown by known methods. The present invention allows easy detection of the presence or absence of specific fungi in a Kampo crude drug product, crude drug, or antibacterial food. The solvent used for the preparation of the solution of the test sample such as a Kampo crude drug product, crude drug, or antibacterial food may be, for example, a phosphate buffer, a peptone salt buffer, or a liquid medium used for cultivation.

EXAMPLES

Example 1

The effect of the addition of acid clay or activated clay to the culture medium was examined as follows. Using Sammotsuogonto and Daijokito, which are Kampo extracts as the test samples, *Staphylococcus aureus* IFO 13276 was added to soybean-casein-digest broth media (hereinafter referred to as SCD media) containing acid clay or activated clay under the conditions listed in Table 1, thereby investigating the growth of the target bacterium in the culture media having different compositions, in accordance with the "Medium Performance Test and Growth Inhibitor Verification Test" under the microbial limit test method described in Japanese Pharmacopoeia. After the proliferating cultivation, the culture was spread and cultured on a Vogel-Johnson agar, and investigated for the qualitative response of the *Staphylococcus aureus*.

Conventional Example 1

As a conventional example, a culture test was conducted in the same manner as in Examples, except that a medium containing activated carbon was used.

Comparative Examples 1-1 to 1-3

As comparative examples, culture tests were conducted using media containing the test sample and/or the target bacterium without activated carbon and activated clay.

Comparative Examples 1-4 and 1-5

As comparative examples, culture tests were conducted in the same manner as in Examples, except that media containing SEPABEADS SP-700(trademark: manufactured by Mitsubishi Chemical Corporation), which is a typical ion adsorbent, were used.

Cultures showed colony formation and qualitative response were rated as ○, colony formation only or weak qualitative response as Δ, and no colony formation as x. The results are listed in Table 1.

TABLE 1

| | Medium composition | Loading (% by weight) | Cultivation Rating | |
|---|---|---|---|---|
| | | | Sammotsuogonto | Daijokito |
| Conventional Example 1-1 | Medium containing activated carbon (for chromatography) | 5 | ○ | ○ |
| Conventional Example 1-2 | | 1 | X | X |

TABLE 1-continued

| | Medium composition | Loading (% by weight) | Cultivation Rating Sammotsuogonto | Daijokito |
|---|---|---|---|---|
| Conventional Example 1-3 | Medium containing activated carbon | 5 | ○ | ○ |
| Conventional Example 1-4 | (powder) | 1 | X | X |
| Conventional Example 1-5 | Medium containing activated carbon | 5 | ○ | X |
| Conventional Example 1-6 | (granules) | 1 | X | X |
| Example 1-1 | Medium containing | 10 | ○ | Δ |
| Example 1-2 | activated clay | 5 | ○ | Δ |
| Example 1-3 | Medium containing | 10 | ○ | X |
| Example 1-4 | acid clay | 5 | ○ | X |
| Comparative Example 1-1 | Medium + test sample | — | X | X |
| Comparative Example 1-2 | Medium + target bacterium | — | ○ | ○ |
| Comparative Example 1-3 | Medium + test sample + target bacterium | — | X | X |
| Comparative Example 1-4 | Medium containing ion absorbent | 5 | X | ○ |
| Comparative Example 1-5 | | 1 | X | X |

The results listed in Table 1 indicate that the target bacterium did not grow in the ordinary media containing a Kampo extract as the test sample. On the other hand, in the examples using activated clay-containing media, the target bacterium grew as in the case of the conventional examples using activated carbon (powder). In the examples using acid clay-containing media, the target bacterium grew by the Kampo extracts. Accordingly, it was confirmed that the addition of acid clay or activated clay allows adequate growth of the target bacterium in the antibacterial Kampo extracts. In some examples, the granular activated carbon and ion adsorbent were not effective against the Kampo extracts.

Example 2 and Comparative Example 2

The effect of activated clay-containing culture media with different test samples was examined as follows. Using Gorinsan and Ryutanshakanto, which are Kampo extracts, as the test samples, *Staphylococcus aureus* IFO 13276 was added to culture media (basal medium: SCD medium) containing activated clay in amounts listed in Table 2 below. The test and evaluation were carried out in the same manner as in Example 1.

Cultures showed colony formation and qualitative response were rated as ○, colony formation only or weak qualitative response as Δ, and no colony formation as x. The results are listed in Table 2.

TABLE 2

| | Test sample | Loading of activated clay (% by weight) | Cultivation Rating |
|---|---|---|---|
| Example 2-1 | Gorinsan | 10 | ○ |
| Comparative Example 2-1 | | 0 | X |
| Example 2-2 | Ryutanshakanto | 10 | ○ |
| Comparative Example 2-2 | | 0 | X |

The results listed in Table 2 indicate that the addition of activated clay to the culture medium repressed the antibacterial activity of Gorinsan and Ryutanshakanto to allow the growth of the target bacterium.

Conventional Example 3, Example 3, and Comparative Example 3

The effect of culture media containing activated clay and activated carbon was examined as follows. Using Junchoto, Gorinsan, Ryutanshakanto, Tsudosan, and Daijokito, which are Kampo extracts, as the test samples, *Staphylococcus aureus* IFO 13276 was added to culture media (basal medium: SCD medium) containing activated clay and activated carbon in amounts listed in Table 3 below. The test and evaluation were carried out in the same manner as in Example 1.

Cultures showed colony formation and qualitative response were rated as ○, colony formation only or weak qualitative response as Δ, and no colony formation as x. The results are listed in Table 3.

TABLE 3

| | Additive sample | Loading of activated carbon (% by weight) | Loading of activated clay (% by weight) | Cultivation Rating |
|---|---|---|---|---|
| Conventional Example 3-1 | Junchoto | 3 | 0 | Δ |
| Example 3-1 | | 3 | 5 | ○ |
| Example 3-2 | | 3 | 10 | ○ |
| Comparative Example 3-1 | | 0 | 0 | X |
| Conventional Example 3-2 | Gorinsan | 3 | 0 | Δ |
| Example 3-3 | | 3 | 5 | ○ |
| Example 3-4 | | 3 | 10 | ○ |
| Comparative Example 3-2 | | 0 | 0 | X |
| Conventional Example 3-3 | Ryutanshakanto | 3 | 0 | Δ |
| Example 3-5 | | 3 | 5 | ○ |
| Example 3-6 | | 3 | 10 | ○ |
| Comparative Example 3-3 | | 0 | 0 | X |
| Conventional Example 3-4 | Tsudosan | 3 | 0 | Δ |

TABLE 3-continued

| Additive sample | | Loading of activated carbon (% by weight) | Loading of activated clay (% by weight) | Cultivation Rating |
|---|---|---|---|---|
| Example 3-7 | | 3 | 5 | ◯ |
| Example 3-8 | | 3 | 10 | ◯ |
| Comparative Example 3-4 | | 0 | 0 | X |
| Conventional Example 3-5 | Daijokito | 3 | 0 | ◯ |
| Example 3-9 | | 3 | 5 | ◯ |
| Example 3-10 | | 3 | 10 | ◯ |
| Comparative Example 3-5 | | 0 | 0 | X |

The results listed in Table 3 indicate that the target bacterium more markedly grew in the examples using culture media containing activated clay and activated carbon, in comparison with the case using activated carbon alone. It was thus confirmed that the combination of activated clay and activated carbon more effectively represses the antibacterial activity of the test samples.

Example 4 and Comparative Example 4

Using Keishibukuryogan, Yokukansan, and Daikenchuto as the test samples, *Staphylococcus aureus* IFO 13276 was added to culture media (basal medium: SCD medium) containing activated clay and activated carbon in amounts listed in Table 4 below. The test and evaluation were carried out in the same manner as in Example 1.

Cultures showed colony formation and qualitative response were rated as ◯, colony formation only or weak qualitative response as Δ, and no colony formation as x. The results are listed in Table 4.

TABLE 4

| Additive sample | | Loading of activated carbon (% by weight) | Loading of activated clay (% by weight) | Cultivation Rating |
|---|---|---|---|---|
| Comparative Example 4-1 | Keishibukuryogan | 0 | 0 | X |
| Conventional Example 4-1 | | 1 | 0 | X |
| Example 4-1 | | 1 | 3 | ◯ |
| Comparative Example 4-2 | Yokukansan | 0 | 0 | Δ |
| Conventional Example 4-2 | | 1 | 0 | Δ |
| Example 4-2 | | 1 | 3 | ◯ |
| Comparative Example 4-3 | Daikenchuto | 0 | 0 | X |
| Conventional Example 4-3 | | 1 | 0 | Δ |
| Example 4-3 | | 1 | 3 | ◯ |

The results listed in Table 4 indicate that the qualitative response owing to the favorable growth of the target bacterium was constantly observed in the examples using the culture media containing activated clay and activated carbon, but stable qualitative response was not observed in the cases using activated carbon alone or no additive. It was thus confirmed that the combination of activated clay and activated carbon more effectively represses the antibacterial activity of the test samples, thereby providing stable test results.

Example 5 and Comparative Example 5

Using Keishibukuryogan, Yokukansan, and Daikenchuto as the test samples, *Staphylococcus aureus* IFO 13276 was added to culture media (basal medium: SCD medium) containing activated clay and activated carbon in amounts listed in Table 5 below. The test and evaluation were carried out in accordance with United States Pharmacopeia 30, <62> MICROBIOLOGICAL EXAMINATION OF NONSTERILE PRODUCTS: TESTS FOR SPECIFIED MICROORGANISMS.

Cultures showed colony formation and qualitative response were rated as ◯, colony formation only or weak qualitative response as Δ, and no colony formation as x. The results are listed in Table 5.

TABLE 5

| Additive sample | | Loading of activated carbon (% by weight) | Loading of activated clay (% by weight) | Cultivation Rating |
|---|---|---|---|---|
| Comparative Example 5-1 | Keishibukuryogan | 0 | 0 | X |
| Conventional Example 5-1 | | 1 | 0 | Δ |
| Example 5-1 | | 1 | 3 | ◯ |
| Comparative Example 5-2 | Yokukansan | 0 | 0 | Δ |
| Conventional Example 5-2 | | 1 | 0 | Δ |
| Example 5-2 | | 1 | 3 | ◯ |
| Comparative Example 5-3 | Daikenchuto | 0 | 0 | X |
| Conventional Example 5-3 | | 1 | 0 | Δ |
| Example 5-3 | | 1 | 3 | ◯ |

The results listed in Table 5 indicate that the qualitative response owing to the favorable growth of the target bacterium was constantly observed in the examples using the culture media containing activated clay and activated carbon, but stable qualitative response was not observed in the cases using activated carbon alone or no additive. It was thus confirmed that the combination of activated clay and activated carbon more effectively represses the antibacterial activity of the test samples, thereby providing stable test results.

Comparative Example 6, Example 6 and Conventional Example 6

The influence of the growth of bacteria in the culture media each containing 5% by weight of activated carbon (powder) alone or 5% by weight of activated clay alone was examined as follows. According to the "Medium Performance Test and Growth Inhibitor Verification Test" under the microbial limit test method described in Japanese Pharmacopoeia, the growth of target bacteria in SCD media alone and SCD media containing 5% by weight of activated clay or activated carbon was investigated. The bacterial species tested were *Staphylococcus aureus* IFO 13276 and *Pseudomonas aeruginosa* IFO 13275. After the proliferating cultivation, the cultures of the *Staphylococcus aureus* were spread and cultured on Vogel-Johnson agar and the cultures of the *Pseudomonas aeruginosa* were spread and cultured on NAC agar media, respectively, and were investigated for the qualitative response of *Staphylococcus aureus* or *Pseudomonas aeruginosa*.

Cultures showed colony formation and qualitative response were rated as ◯, colony formation only or weak qualitative response as Δ, and no colony formation as x. Ten samples were tested in each of the examples, comparative examples, and conventional examples. The results are listed in Table 6 below.

TABLE 6

|  |  | Comparative Example 6-1 Medium alone | Comparative Example 6-2 | Example 6-1 Medium + activated clay | Example 6-2 | Conventional Example 6-1 Medium + activated carbon | Conventional Example 6-2 |
|---|---|---|---|---|---|---|---|
|  |  | Staphylococcus aureus | Pseudomonas aeruginosa | Staphylococcus aureus | Pseudomonas aeruginosa | Staphylococcus aureus | Pseudomonas aeruginosa |
| Sample No. | No. 1 | ○ | ○ | ○ | ○ | Δ | ○ |
|  | No. 2 | ○ | ○ | ○ | ○ | ○ | ○ |
|  | No. 3 | ○ | ○ | ○ | ○ | ○ | ○ |
|  | No. 4 | ○ | ○ | ○ | ○ | Δ | ○ |
|  | No. 5 | ○ | ○ | ○ | ○ | Δ | ○ |
|  | No. 6 | ○ | ○ | ○ | ○ | Δ | ○ |
|  | No. 7 | ○ | ○ | ○ | ○ | Δ | ○ |
|  | No. 8 | ○ | ○ | ○ | ○ | ○ | ○ |
|  | No. 9 | ○ | ○ | ○ | ○ | ○ | ○ |
|  | No. 10 | ○ | ○ | ○ | ○ | ○ | ○ |

The results listed in Table 6 indicate that the colony formation of *Staphylococcus aureus* was weak on some media containing 5% by weight of activated carbon. This is likely due to that excessive portions of activated carbon adsorb the components of the media to adversely affect the microbial growth. On the other hand, the addition of activated clay gave no adverse effect, even when the loading was increased to 10% by weight.

Example 7, Comparative Example 7, and Conventional Example 7

The influences of activated carbon and activated clay on culture media were closely examined as follows. According to the microbial limit test method described in Japanese Pharmacopoeia, the bacterial concentrations in SCD media alone and SCD media containing activated clay and/or activated carbon in amounts listed in Table 7 below were measured after shaking culture for 24 hours. As the target bacteria, *Staphylococcus aureus* IFO 13276 and *Pseudomonas aeruginosa* IFO 13275 were used. The initial number of the bacteria was about 100 cfu. The results are listed in Table 7, wherein "%" refers to "% by weight".

TABLE 7

| | Target bacterium | Culture medium composition | Number of bacterium (log10 ((bacterial concentration) cfu/ml)) |
|---|---|---|---|
| Example 7-1 | *Staphylococcus aureus* | SCD medium + 3% activated carbon + 5% activated clay | 6.9 |
| Comparative Example 7-1 | | SCD medium alone | 6.7 |
| Example 7-2 | | SCD medium + 5% activated clay | 7.9 |
| Conventional Example 7-1 | | SCD medium + 3% activated carbon | 4.2 |
| Example 7-3 | *Pseudomonas aeruginosa* | SCD medium + 3% activated carbon + 5% activated clay | 9.1 |
| Comparative Example 7-2 | | SCD medium alone | 8.8 |
| Example 7-4 | | SCD medium + 5% activated clay | 9.2 |
| Conventional Example 7-2 | | SCD medium + 3% activated carbon | 8.6 |

The results listed in Table 7 indicate that the proliferation potencies of *Staphylococcus aureus* and *Pseudomonas aeruginosa* in the media containing 3% by weight of activated carbon and 5% by weight of activated clay were about the same as those in the media with no additive. On the other hand, the proliferation potency of *Staphylococcus aureus* was particularly low in the media containing activated carbon alone, indicating that the addition of activated clay suppresses the deterioration of the proliferation potency caused by the addition of activated carbon.

Example 8 and Comparative Example 8

Using Keishibukuryogan as the test sample, under the assumption of microbial limit test described in United States Pharmacopeia, formation of typical colonies in test sample solutions was examined in accordance with United States Pharmacopeia 28, <61> MICROBIAL LIMIT TESTS. The test sample solutions were a SCD medium containing 3% by weight of activated carbon and 5% by weight of activated clay (ISCD medium), a SCD medium with no additive, and a SCD medium containing 0.5% by weight of lecithin and 4.0% by weight of polysorbate 20 (LPSCD medium), the sample concentration during cultivation was 0.01 g/mL, and the target bacterium was *Staphylococcus aureus* ATCC 6538.

Cultures showed colony formation and qualitative response were rated as ○, colony formation only or weak qualitative response as Δ, and no colony formation as x. The results are listed in Table 8 below.

TABLE 8

| Test sample solution and medium | | With test sample | Sample solution alone | Conclusion |
|---|---|---|---|---|
| Example 8-1 | ISCD | ○ | X | No influence of antibacterial substance |
| Comparative Example 8-1 | SCD | X | X | Influenced by antibacterial substance |
| Comparative Example 8-2 | LPSCD | X | X | Influenced by antibacterial substance |

The results listed in Table 8 indicate that no typical colony was formed in the culture using the LPSCD medium, which is an inactivated culture medium included in United States Pharmacopeia, as the test sample solution, suggesting that the influence of antibacterial substances was not repressed. On the other hand, typical colonies were formed in the culture using the ISCD medium containing activated clay and activated carbon, suggesting that the influence of antibacterial substances was repressed.

Example 9 and Comparative Example 9

Using Keishibukuryogan as the test sample, *Salmonella enterica* spp. *enterica* serotype abony ACM 5080 was added to the media (basal medium: SCD medium) containing activated clay and activated carbon in amounts listed in Table 9 below. The test and evaluation were carried out in accordance with United States Pharmacopeia 30, <62> MICROBIOLOGICAL EXAMINATION OF NONSTERILE PRODUCTS: TESTS FOR SPECIFIED MICROORGANISMS.

Cultures showed colony formation and qualitative response were rated as ○, colony formation only or weak qualitative response as Δ, and no colony formation as x. The results are listed in Table 9.

TABLE 9

| | Test sample | Loading of activated carbon (% by weight) | Loading of activated clay (% by weight) | Cultivation Rating |
|---|---|---|---|---|
| Comparative Example 9-1 | Keishibukuryogan | 0 | 0 | X |
| Conventional Example 9-1 | | 1 | 0 | X |
| Example 9-1 | | 1 | 3 | ○ |
| Example 9-2 | | 1 | 5 | ○ |
| Example 9-3 | | 3 | 5 | ○ |

The results listed in Table 9 indicate that the target bacterium grew in the culture media of examples containing activated clay and activated carbon, but they did not grow in the media containing activated carbon alone. These facts suggest that the combination of activated clay and activated carbon more effectively represses the antibacterial activity of the test sample.

Example 10 and Comparative Example 10

The growth of a target bacterium in media containing a food as the test sample was examined as follows, wherein the test sample was Japanese horseradish or tea leaves. 10 g, 1 g, and 0.1 g of a Japanese horseradish paste or tea leaves, (which had been subjected to autoclave sterilization to prevent contamination), were added to a peptone buffer respectively thereby making 100 mL of 10-fold, 100-fold, and 1000-fold diluted test sample solutions. 10 mL of the respective test sample solutions was individually added to 90 mL portions of SCD media, SCD media containing lecithin and polysorbate (SCDLP medium), and SCD media containing 3% by weight of activated carbon and 5% by weight of activated clay (ISCD medium), and the growth of the test bacterium was investigated in accordance with the "Medium Performance Test and Growth Inhibitor Verification Test" under the microbial limit test method described in Japanese Pharmacopoeia. The bacterium tested was *Staphylococcus aureus* IFO 13276, and the test and evaluation were carried out in the same manner as in Example 1.

Cultures showed colony formation and qualitative response were rated as ○, colony formation only or weak qualitative response as Δ, and no colony formation as x. The results are listed in Table 10 below.

TABLE 10

| | | Comparative Example 10-1 SCD medium | Comparative Example 10-2 SCDLP medium | Example 10 ISCD medium |
|---|---|---|---|---|
| Test sample solution | Japanese horseradish 10-fold diluted solution | X | X | ○ |
| | Japanese horseradish 100-fold diluted solution | ○ | ○ | ○ |
| | Japanese horseradish 1000-fold diluted solution | ○ | ○ | ○ |
| | Tea leaf 10-fold diluted solution | X | X | ○ |
| | Tea leaf 100-fold diluted solution | Δ | ○ | ○ |
| | Tea leaf 1000-fold diluted solution | ○ | ○ | ○ |

The results listed in Table 10 indicate that the target bacterium formed no colony in the SCD and SCDLP media containing the 10-fold diluted solutions of Japanese horseradish and tea leaves with high concentration, suggesting that the influence of antibacterial substances was not repressed. On the other hand, colonies were formed in all the mixtures of the diluted solutions and the ISCD media containing activated clay and activated carbon, suggesting that the influence of antibacterial substances was repressed. These facts indicate that the culture medium of the present invention adsorbs and reduces antibacterial substances contained in Japanese horseradish and tea leaves as well as those contained in Kampo extracts, thereby repressing their antibacterial activity. Accordingly, the culture medium is applicable to the improvement of food microbial test.

Example 11 and Comparative Example 11

The growth of a target bacterium in media containing a dry spice as the test sample was examined as follows. 10 g, 5 g, and 0.5 g of turmeric powder, pepper powder, and dry basil leaves were made into 100 mL solutions, from which 10-fold, 20-fold, and 200-fold diluted solutions were prepared. 10 mL of the respective test sample solutions were individually added to 90 mL portions of SCD media containing 7.5% of salt, which are listed in the microbial limit test method for crude drugs described in Japanese Pharmacopoeia, SCD media containing 7.5% of salt, 3% by weight of activated carbon, and 5% by weight of activated clay (SCDAA media containing 7.5% of salt), and SCDB media containing 7.5% of salt and 5% by weight of activated clay (SCDA media containing 7.5% of salt). The growth of the test bacterium was investigated in accordance with the "Medium Performance Test and Growth Inhibitor Verification Test" under the microbial limit test method described in Japanese Pharmacopoeia. The bacterium tested was *Staphylococcus aureus* IFO 13276, and the test and evaluation were carried out in the same manner as in Example 1.

Cultures showed colony formation and qualitative response were rated as ○, colony formation only or weak qualitative response as Δ, and no colony formation as x. The results are listed in Table 11 below.

The results listed in Table 11 indicate that the target bacterium formed no colony in the SCD media containing 7.5% of salt and the 10-fold or 20-fold diluted solution of turmeric powder, pepper powder, or dry basil leaves, suggesting that the influence of antibacterial substances was not repressed. On the other hand, colonies were formed in all the mixtures of the dry basil leaves diluted solutions in the SODA media containing 7.5% of salt and activated clay and all the mixtures in the SCDAA media containing 7.5% of salt, activated clay, and activated carbon, suggesting that the influence of antibacterial substances was repressed. These facts indicate that the culture medium of the present invention adsorbs and reduces antibacterial substances contained in a dry spice as well as those contained in Kampo extracts, thereby inhibiting their antibacterial activity. Accordingly, the culture medium is applicable to the improvement of food microbial test.

Example 12 and Comparative Example 12

The growth of target bacteria in media containing an antibiotic as the test sample was examined as follows. Chloramphenicol was added to SCD media which are described in the microbial limit test method in Japanese Pharmacopoeia, SCD media containing 3% by weight of activated carbon and 5% by weight of activated clay (ISCD media), lactose broth media (hereinafter referred to as LB media), and LB media containing 3% by weight of activated carbon and 5% by weight of activated clay (ILB media) at concentrations of 250 mg/L, 50 mg/L, 5 mg/L, 0.5 mg/L, and 0.05 mg/L respectively. The growth of the test bacteria was investigated in accordance with the "Medium Performance Test and Growth Inhibitor Verification Test" under the microbial limit test method described in Japanese Pharmacopoeia. The bacteria tested were *Staphylococcus aureus* IFO 13276 for the SCD and ISCD media, and *Escherichia coli* IFO 3972 for the LB and ILB media. After the proliferating cultivation, the cultures of the *Staphylococcus aureus* and *Escherichia coli* were spread and cultured on Vogel-Johnson agar media (*Staphylococcus aureus*) and MacConkey agar media (*Escherichia coli*), respectively, and investigated for the qualitative response.

Cultures showed colony formation and qualitative response were rated as ○, colony formation only or weak qualitative response as Δ, and no colony formation as x. The results are listed in Table 12 below, wherein "%" refers to "% by weight".

TABLE 11

| | | Comparative Example 11-1 SCD medium containing 7.5% of salt | Example 11-1 SCDAA medium containing 7.5% of salt | Example 11-2 SCDA medium containing 7.5% of salt |
|---|---|---|---|---|
| Turmeric powder | Addition of 10-fold diluted solution (concentration in medium: 1 g/100 mL) | X | ○ | X |
| | Addition of 20-fold diluted solution (concentration in medium: 0.5 g/100 mL) | X | ○ | X |
| | Addition of 200-fold diluted solution (concentration in medium: 0.05 g/100 mL) | ○ | ○ | ○ |
| Pepper powder | Addition of 10-fold diluted solution (concentration in medium: 1 g/100 mL) | X | ○ | X |
| | Addition of 20-fold diluted solution (concentration in medium: 0.5 g/100 mL) | X | ○ | X |
| | Addition of 200-fold diluted solution (concentration in medium: 0.05 g/100 mL) | ○ | ○ | ○ |
| Dry basil leaves | Addition of 10-fold diluted solution (concentration in medium: 1 g/100 mL) | X | ○ | ○ |
| | Addition of 20-fold diluted solution (concentration in medium: 0.5 g/100 mL) | X | ○ | ○ |
| | Addition of 200-fold diluted solution (concentration in medium: 0.05 g/100 mL) | ○ | ○ | ○ |

TABLE 12

| Chloramphenicol concentration (mg/L) | Comparative Example 12-1 *Staphylococcus aureus* SCD medium | Example 12-1 ISCD (3% activated carbon + 5% activated clay) medium | Comparative Example 12-2 *Escherichia coli* LB medium | Example 12-2 ILB (3% activated carbon + 5% activated clay) medium |
|---|---|---|---|---|
| 250 | X | X | — | — |
| 50 | X | ○ | — | — |
| 5 | X | ○ | X | ○ |
| 0.5 | ○ | ○ | X | ○ |
| 0.05 | ○ | ○ | ○ | ○ |

The results listed in Table 12 indicate that *Staphylococcus aureus* and *Escherichia coli* formed colonies and showed qualitative responses after cultivation in the ISCD and ILB media containing antibiotics at concentrations 100 times higher than ordinary SCD and LB media, suggesting that the influence of the antibiotics was repressed. These facts indicate that the culture medium of the present invention represses the antibacterial activity of samples containing antibiotics as well as that of Kampo extracts. Accordingly, the culture medium is applicable to the improvement of microbial test on general drugs.

Example 13

The microbial growth in media containing activated clay and activated carbon at a ratio of 1% or 2% of activated carbon with reference to 5% of activated clay was examined as follows. Using Junchoto, Gorinsan, Ryutanshakanto, Tsudosan, and Daijokito, which are Kampo extracts, as the test samples, the test and evaluation were carried out in the same manner as in Example 3.

Cultures showed colony formation and qualitative response were rated as ○, colony formation only or weak qualitative response as Δ, and no colony formation as x. The results are listed in Table 13 below.

TABLE 13

| | Test sample | Loading of activated carbon (% by weight) | Loading of activated clay (% by weight) | Rating |
|---|---|---|---|---|
| Example 13-1 | Junchoto | 1 | 5 | ○ |
| Example 13-2 | | 2 | 5 | ○ |
| Example 13-3 | Gorinsan | 1 | 5 | ○ |
| Example 13-4 | | 2 | 5 | ○ |
| Example 13-5 | Ryutanshakanto | 1 | 5 | ○ |
| Example 13-6 | | 2 | 5 | ○ |
| Example 13-7 | Tsudosan | 1 | 5 | ○ |
| Example 13-8 | | 2 | 5 | ○ |
| Example 13-9 | Daijokito | 1 | 5 | ○ |
| Example 13-10 | | 2 | 5 | ○ |

The results listed in Table 13 indicate that the target bacterium sufficiently grew in the media containing 5% by weight of activated clay and activated carbon even at a content of 1% by weight, suggesting that the antibacterial activity of the test samples was effectively repressed.

The invention claimed is:

1. A microbial culture medium for growing a target bacterium contained in an antibacterial test sample, which comprises a basal medium for microbial culture, and activated clay and activated carbon contained in the basal medium, wherein the amount of activated clay is 3 to 10% by weight of the culture medium and the amount of activated carbon is 1% by weight or more and less than 5% by weight of the basal medium, and wherein the antibacterial test sample is selected from the group consisting of Kampo crude drug products, crude drugs, and antibacterial foods.

2. The microbial culture medium of claim 1, wherein the antibacterial test sample is selected from the group consisting of Sammotsuogonto, Daijokito, Gorinsan, Junchoto, Tsudosan, Yokukansan and Daikenchuto.

3. A microbial culture method for growing a target bacterium contained in an antibacterial test sample using a microbial culture medium, which comprises adding activated clay and activated carbon into a solution of the test sample, wherein the amount of activated clay is 3 to 10% by weight of the solution of the test sample and the amount of activated carbon is 1% by weight or more and less than 5% by weight of the solution of the test sample, and wherein the antibacterial test sample is selected from the group consisting of Kampo crude drug products, crude drugs, and antibacterial foods.

4. The microbial culture method of claim 3, wherein the antibacterial test sample is selected from the group consisting of Sammotsuogonto, Daijokito, Gorinsan, Junchoto, Tsudosan, Yokukansan and Daikenchuto.

5. A microbial culture medium for growing a target bacterium contained in an antibacterial test sample, which consists essentially of a basal medium for microbial culture, activated clay contained in the basal medium, and activated carbon contained in the basal medium, wherein the amount of activated clay is 3 to 10% by weight of the culture medium and the amount of activated carbon is 1% by weight or more and less than 5% by weight of the basal medium, and wherein the antibacterial test sample is selected from the group consisting of Kampo crude drug products, crude drugs, and antibacterial foods.

6. The microbial culture medium of claim 5, wherein the antibacterial test sample is selected from the group consisting of Sammotsuogonto, Daijokito, Gorinsan, Junchoto, Tsudosan, Yokukansan and Daikenchuto.

* * * * *